United States Patent [19]
Robichaud

[11] Patent Number: 4,794,920
[45] Date of Patent: Jan. 3, 1989

[54] BIRTH CONTROL DEVICE

[76] Inventor: David M. Robichaud, 15 Edgehill Road, Islington, Ontario, Canada, M9A 4N1

[21] Appl. No.: 74,300

[22] Filed: Jul. 14, 1987

[51] Int. Cl.⁴ ............................................. A61F 13/00
[52] U.S. Cl. .................... 128/844; 604/347; 604/349
[58] Field of Search ............... 128/131, 132 R, 79, 128/98, 138 R; 604/252, 347, 349, 353

[56] References Cited

U.S. PATENT DOCUMENTS

| | | | |
|---|---|---|---|
| D. 254,808 | 4/1980 | Meldaul | 604/349 |
| 2,123,343 | 0/1938 | Rightsell | 128/132 R |
| 2,305,453 | 0/1942 | Martos | 128/132 R |
| 2,406,600 | 0/1946 | Forestiere | 128/630 |
| 2,548,149 | 0/1951 | Fowler, Jr. | 604/347 |
| 2,591,783 | 0/1952 | Craddock | 128/131 |
| 2,904,041 | 9/1959 | Brown | 128/132 R |
| 3,536,066 | 0/1970 | Ludwig | 128/132 R |
| 3,677,225 | 7/1972 | Czirely | 128/132 R |
| 3,759,254 | 0/1973 | Clark | 604/349 |
| 4,004,591 | 1/1977 | Freimark | 604/330 |
| 4,354,494 | 10/1982 | Hogin | 128/132 R |
| 4,664,104 | 5/1987 | Jaicks | 128/132 R |

FOREIGN PATENT DOCUMENTS

| | | |
|---|---|---|
| 254211 | 1/1912 | Fed. Rep. of Germany . |
| 267218 | 1/1913 | Fed. Rep. of Germany . |

*Primary Examiner*—Robert A. Hafer
*Assistant Examiner*—Charles H. Sam
*Attorney, Agent, or Firm*—Ridout & Maybee

[57] ABSTRACT

A birth control device comprises an oversized sheath portion fitting loosely about the male organ and a flange about the open end of the sheath for retaining the open end of the device outside the woman's body.

4 Claims, 1 Drawing Sheet

BIRTH CONTROL DEVICE

The present invention is a birth control or prophylactic device for use by male and female partners during coitus.

Presently available prophylactic devices for men comprise various types of condoms which are sheaths made of rubber or a synthetic material which is very thin yet strong enough to prevent the formation of holes therein during use. These devices are elastic and designed to fit tightly on the male organ during coitus. Condoms are also available which are made of animal skin or tissue which is generally less elastic than the rubber or synthetic materials and thus, do not fit as tightly about the male organ. However, the general principle of operation for all condoms presently available is the same, namely that the device frictionally or elastically engages the male organ during coitus to provide a receptacle for seminal fluid.

One of the presently available prophylactic devices for women is a diaphragm which is positioned within the vagina to provide a physical barrier to sperm at the entrance to the uterus.

The present invention comprises an improvement of the condom and diaphragm by providing a sheath of a thin flexible impermeable material of moderate elasticity which is designed to fit loosely about the erect male organ for insertion of the device into the vagina. The device conforms to the shape of the vagina and movement of the male organ relative to the sheath of the device is not restricted. In fact it is preferred to provide the interior of the sheath of the device with lubricant to facilitate movement by reducing friction between the male organ and the sheath. The device of the invention is kept in place by means of a flange about or a widening of the open end of the sheath. The flange portion of the device comprises at least an outer peripheral portion of a semi-rigid but compliant material proportional to retain the open end of the device outside the woman's body during coitus.

The advantages of the present device include ease of use and comfort, as well as a lower risk of failure due to a tearing of the material of the sheath. Because the present device does not rely on the transmission of sensation through the material of the sheath, it can be made of a somewhat thicker and stronger material than is used in conventional condoms.

The drawings are not meant to accurately reflect relative dimensions of the components of the invention, but rather to illustrate the principles of operation for the two preferred embodiments described below.

The birth control device of the invention comprises a sheath 10 sized to fit loosely about the erect male organ. The sheath 10 is preferably made of a thin flexible impermeable material, but need not be as thin or elastic as the materials used in presently available condoms. The sheath 10 of the invention is intended to accommodate movement of the male organ during coitus relative to it in contrast to the operation of condoms presently available wherein the sheath and the male organ move in unison. The structure of the sheath 10 in accordance with the invention allows for easier application of the device and is more comfortable for both partners, than is the case for conventional condoms.

Prior devices are known which comprised a closed end tubular structure of a rigid material or a fairly stiff compliant plastic so that the device would be held by the vagina. These devices were unsatisfactory at least due to the physical difficulty encountered through the creation of suction and compression effects with such devices during their use. The present device conforms to the shape of the vagina to allow for natural movement during coitus without the creation of suction or compression within the device.

Figure 1:
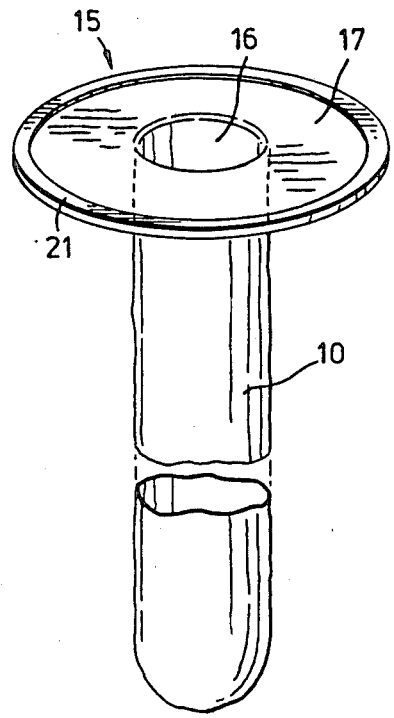
FIG. 1 is a perspective view of one preferred embodiment of the invention.
Figure 2:
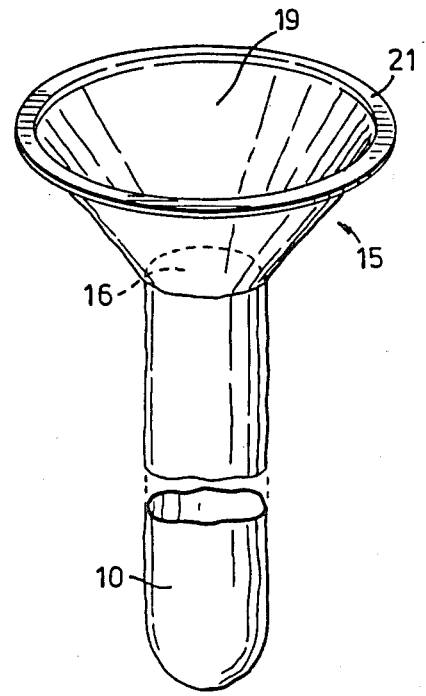
FIG. 2 is a perspective view of a second preferred embodiment of the invention.

The device is retained about the opening of the vagina of the woman by flange means 15 about the open end 16 of the sheath 10. The flange means 15 may be any of several structures which function as intended such as a generally flat circular flange 17 (FIG. 1) or a generally frustoconical flange 19 (FIG. 2). The flange means 15 has at least an outer peripheral portion or rim 21 of a semi-rigid compliant material which serves to maintain the flange means 15 extended about the opening of the sheath 10. The rim 21 may be shaped variously to provide the greatest degree of comfort to the users of the device while still performing the intended function, and the rim 21 may be substantially wider than shown in FIG. 1. Thus, in the embodiment shown in FIG. 1, the entire circular flange 17 may be made of a semi-rigid compliant material.

Because the present device operates on a different principle from that of conventionally available condoms, it is preferred that, in addition to a lubricant for the outer surface of the sheath 10, the device of the invention be used in conjunction with a suitable lubricant between the male organ and the inner surface of the sheath 10. This lubricant will facilitate freedom of movement for the partners so that the device serves simply as a receptacle for semen and does not detract from a natural sexual experience.

I claim:

1. A birth control device, comprising:

a sheath defining a closed end and an open end of a thin flexible impermeable material being sized to fit loosely about the erect male organ thereby enabling movement of the male organ relative to the sheath during coitus, said sheath being conformable to the shape of the vagina upon insertion therein; and flange means about the entire open end of the sheath for retaining the open end of the device outside the woman's body during coitus, the flange means being a generally frustoconical widening of the sheath toward its open end having at least an outer peripheral portion of a semi-rigid, compliant material.

2. A device as claimed in claim 1, wherein the sheath is provided with a lubricated inner surface.

3. A device as claimed in claim 1, wherein the flange means is a peripheral flange about the open end of the sheath.

4. A device as claimed in claim 1, wherein the flange means is a peripheral flange of the same material as that of the sheath.

* * * * *